US011113338B2

(12) United States Patent
Mukherji et al.

(10) Patent No.: US 11,113,338 B2
(45) Date of Patent: Sep. 7, 2021

(54) CONCEPTS FOR ITERATIVE AND COLLABORATIVE GENERATION OF DATA REPORTS VIA DISTINCT COMPUTING ENTITIES

(71) Applicant: Optum Services (Ireland) Limited, Dublin (IE)

(72) Inventors: Raja Mukherji, Dublin (IE); Dominik Dahlem, Dublin (IE); Scott D. Johnson, Eden Prairie, MN (US); Michael B. Wentzien, Eden Prairie, MN (US); Joshua L. Taylor, Rocky Hill, CT (US); Thomas R. Gilbertson, Hartford, CT (US); Bruno Ohana, Dublin (IE); Mallory B. Van Horn, Eden Prairie, MN (US); David A. Chennisi, Eden Prairie, MN (US); Yangcheng Huang, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 358 days.

(21) Appl. No.: 16/289,735

(22) Filed: Mar. 1, 2019

(65) Prior Publication Data
US 2020/0278999 A1    Sep. 3, 2020

(51) Int. Cl.
*G06F 16/00*         (2019.01)
*G06F 16/9035*       (2019.01)
(Continued)

(52) U.S. Cl.
CPC ........ *G06F 16/9035* (2019.01); *G06F 16/901* (2019.01); *G06F 16/9038* (2019.01); *G06Q 40/08* (2013.01)

(58) Field of Classification Search
CPC ............... G06F 16/9038; G06F 16/901; G06F 16/9035; G06Q 40/08
See application file for complete search history.

(56) References Cited

U.S. PATENT DOCUMENTS 6,915,254 B1    7/2005  Heinze et al.
7,197,492 B2 *  3/2007  Sullivan ................. G16H 15/00
(Continued)

OTHER PUBLICATIONS

M. Shamim Hossain and Ghulam Muhammad, "Cloud-Based Collaborative Media Service Framework for Healthcare", Hindawi Publishing Corporation, International Journal of Distributed Sensor Networks, vol. 2014, Article ID 858712, pp. 1-11. (Year: 2014).*
(Continued)

*Primary Examiner* — Cheryl Lewis
(74) *Attorney, Agent, or Firm* — Alston & Bird LLP

(57) ABSTRACT

There is a need for solutions that increase efficiency and reliability of medical record processing systems. This need can be addressed, for example, by receiving a free-form primary provider input from a primary provider profile; detecting one or more information deficiencies in the primary provider input, wherein each information deficiency indicates a respective query; for each identified information deficiency of the one or more information deficiencies, identifying a supportive profile associated with the respective information deficiency, causing the supportive profile computing entity associated with the respective supportive provider profile to present an audiovisual interface that includes an indication of the respective query associated with the information deficiency, and receiving a supportive provider input from each supportive provider profile; and generating a collaborative record for the primary provider input based on the primary provider input and each received supportive provider input.

19 Claims, 7 Drawing Sheets

(51) Int. Cl.
  *G06Q 40/08* (2012.01)
  *G06F 16/901* (2019.01)
  *G06F 16/9038* (2019.01)

(56) References Cited

U.S. PATENT DOCUMENTS

| | | | |
|---|---|---|---|
| 7,725,330 | B2 | 5/2010 | Rao et al. |
| 9,542,472 | B2* | 1/2017 | Shah ................... G06Q 50/01 |
| 2012/0022892 | A1* | 1/2012 | Feldman ............... G16H 10/60 |
| | | | 705/3 |
| 2014/0324477 | A1 | 10/2014 | Oez |
| 2015/0081629 | A1* | 3/2015 | Newman ............... G16H 40/67 |
| | | | 707/613 |
| 2016/0110505 | A1* | 4/2016 | Symanski ............. G16H 10/60 |
| | | | 705/3 |
| 2016/0110523 | A1 | 4/2016 | Francois |
| 2016/0259902 | A1* | 9/2016 | Feldman ............... G16H 50/20 |
| 2016/0314277 | A1* | 10/2016 | Korhonen .............. G06F 19/00 |
| 2017/0091388 | A1* | 3/2017 | Zolla ..................... G06F 16/254 |
| 2018/0181718 | A1* | 6/2018 | Zaher ..................... G16H 50/20 |

OTHER PUBLICATIONS

Bharadwaj, "Artificial Intelligence for Medical Billing and Coding," [online], [retrieved from the Internet Jun. 5, 2019], <URL: https://emerj.com/ai-sector-overviews/artificial-intelligence-medical-billing-coding/>, 10 pages.

"3M 'Health Information Systems—360' Promotional Video," YouTube, Feb. 12, 2015, [online], [retrieved from the Internet Jun. 5, 2019], URL: https://www.youtube.com/watch?v=-giq9kdtqfU>, 16 pages.

* cited by examiner

CONCEPTS FOR ITERATIVE AND COLLABORATIVE GENERATION OF DATA REPORTS VIA DISTINCT COMPUTING ENTITIES

BACKGROUND

In certain industries, including the medical industry for example, record processing systems that generate service records (e.g., medical service records) are subject to substantial inefficiencies resulting from incomplete and/or inaccurate data entry by information providers. Often times, a single information provider is tasked with providing complete and accurate data to a record processing system, despite natural gaps in the provider's knowledge about key information only known to other individuals. That information provider may then choose to spend substantial time attempting to locate the proper individual to obtain any unknown but necessary information, or the information provider may make educated guesses as to the unknown information. Because the process of generating and processing service records may include a number of temporally sequential steps, each of which depends on the output of a previous step, a mistake at one step can slow down or render impossible completion of a task of a future step. As a result, many existing medical record processing systems are highly inefficient and suffer from major performance and reliability issues. Such inefficiencies may undermine the ability of existing systems to process medical service claims timely and efficiently and create gaps in medical service delivery and/or processing.

A need thus exists for automated systems for iterative and collaborative generation of data reports in which computing systems are configured to identify proper information providers to provide various pieces of information necessary for the completion of a report.

BRIEF SUMMARY

In general, embodiments of the present invention provide methods, apparatus, systems, computing devices, computing entities, and/or the like for collaborative generation of medical service reports. Certain embodiments utilize systems, methods, and computer program products that enable generating medical service reports using information from a primary provider profile and one or more supportive provider profiles.

In accordance with one aspect, a method is provided. In one embodiment, the method comprises receiving a free-form primary provider input from a primary provider computing entity, wherein the free-form primary provider input comprises a plurality of unstructured data elements and is associated with a primary provider profile; detecting, based at least in part on stored informational requirements data, discrete data elements within the unstructured data elements of the free-form primary provider input and one or more information deficiencies in the primary provider input, wherein each information deficiency indicates a respective query; for each identified information deficiency of the one or more information deficiencies, identifying a supportive profile associated with the respective information deficiency, wherein the supportive profile is associated with a respective computing profile; causing the supportive profile computing entity associated with the respective supportive provider profile to present an audiovisual interface, wherein the audiovisual interface includes an indication of the respective query associated with the information deficiency; and receiving a supportive provider input from the supportive profile computing entity associated with the respective supportive provider profile; and generating a collaborative record for the primary provider input based on the primary provider input and each received supportive provider input.

In accordance with another aspect, a computer program product is provided. The computer program product may comprise at least one computer-readable storage medium having computer-readable program code portions stored therein, the computer-readable program code portions comprising executable portions configured to receive a free-form primary provider input from a primary provider computing entity, wherein the free-form primary provider input comprises a plurality of unstructured data elements and is associated with a primary provider profile; detect, based at least in part on stored informational requirements data, discrete data elements within the unstructured data elements of the free-form primary provider input and one or more information deficiencies in the primary provider input, wherein each information deficiency indicates a respective query; for each identified information deficiency of the one or more information deficiencies, identify a supportive profile associated with the respective information deficiency, wherein the supportive profile is associated with a respective computing profile; cause the supportive profile computing entity associated with the respective supportive provider profile to present an audiovisual interface, wherein the audiovisual interface includes an indication of the respective query associated with the information deficiency; and receive a supportive provider input from the supportive profile computing entity associated with the respective supportive provider profile; and generate a collaborative record for the primary provider input based on the primary provider input and each received supportive provider input.

In accordance with yet another aspect, an apparatus comprising at least one processor and at least one memory including computer program code is provided. In one embodiment, the at least one memory and the computer program code may be configured to, with the processor, cause the apparatus to receive a free-form primary provider input from a primary provider computing entity, wherein the free-form primary provider input comprises a plurality of unstructured data elements and is associated with a primary provider profile; detect, based at least in part on stored informational requirements data, discrete data elements within the unstructured data elements of the free-form primary provider input and one or more information deficiencies in the primary provider input, wherein each information deficiency indicates a respective query; for each identified information deficiency of the one or more information deficiencies, identify a supportive profile associated with the respective information deficiency, wherein the supportive profile is associated with a respective computing profile; cause the supportive profile computing entity associated with the respective supportive provider profile to present an audiovisual interface, wherein the audiovisual interface includes an indication of the respective query associated with the information deficiency; and receive a supportive provider input from the supportive profile computing entity associated with the respective supportive provider profile; and generate a collaborative record for the primary provider input based on the primary provider input and each received supportive provider input.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention. It will be appreciated that the scope of the invention encompasses many potential embodiments in addition to those here summarized, some of which will be further described below.

BRIEF DESCRIPTION OF THE DRAWINGS

Figure 1:
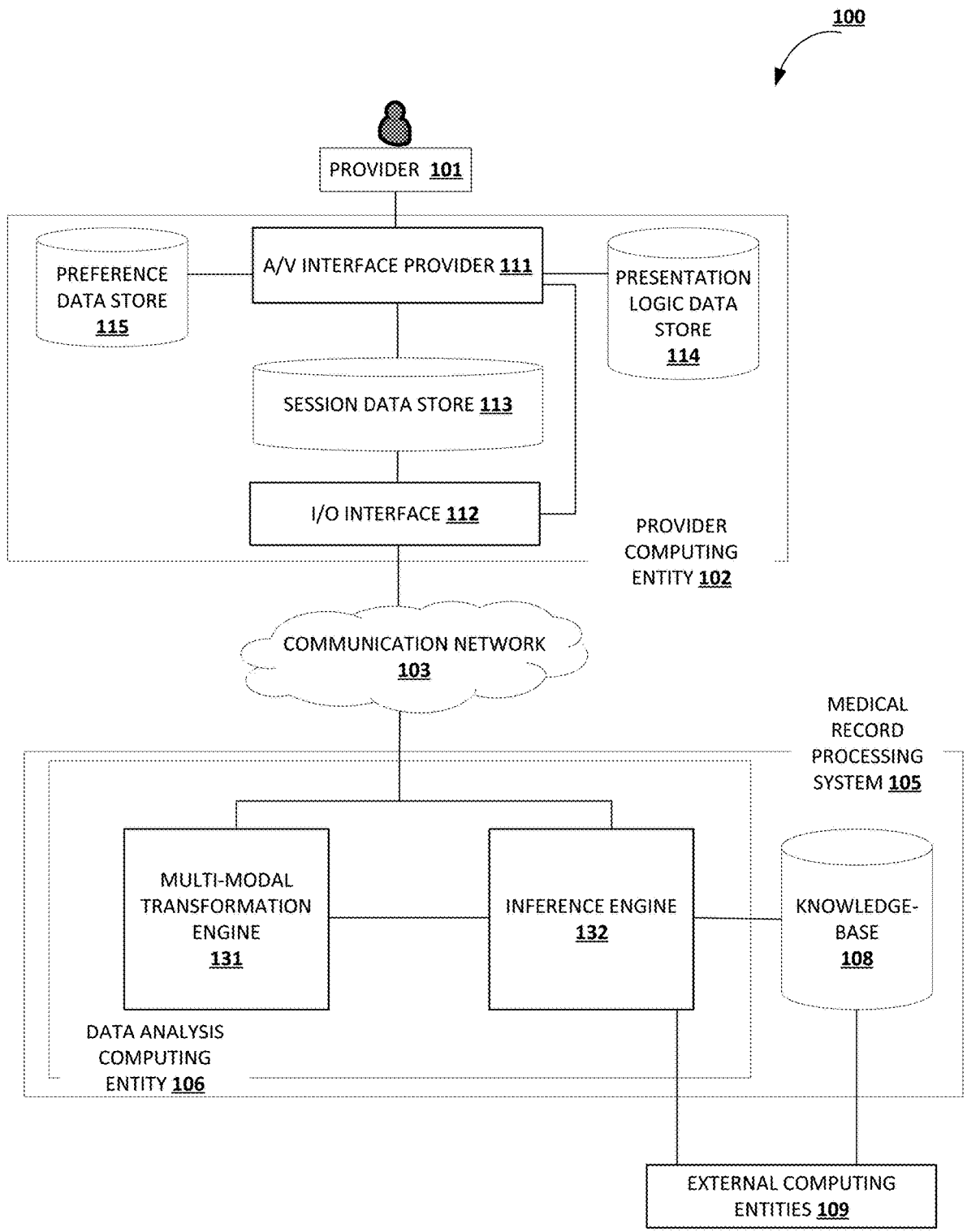

Having thus described the invention in general terms, reference will now be made to the accompanying drawings, which are not necessarily drawn to scale, and wherein:

FIG. 1 is an exemplary overview of a system that can be used to practice embodiments of the present invention.

Figure 2:
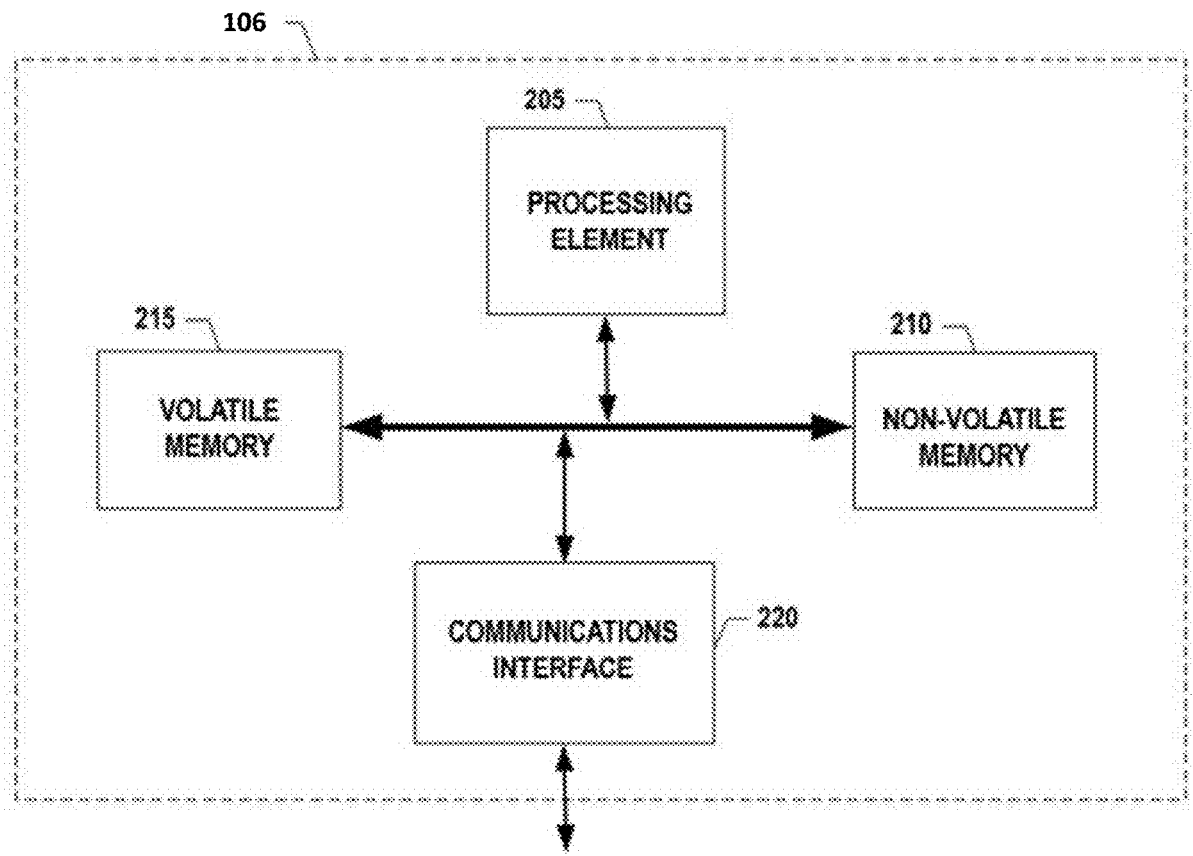

FIG. 2 illustrates an example data analysis computing entity in accordance with some embodiments discussed herein.

Figure 3:
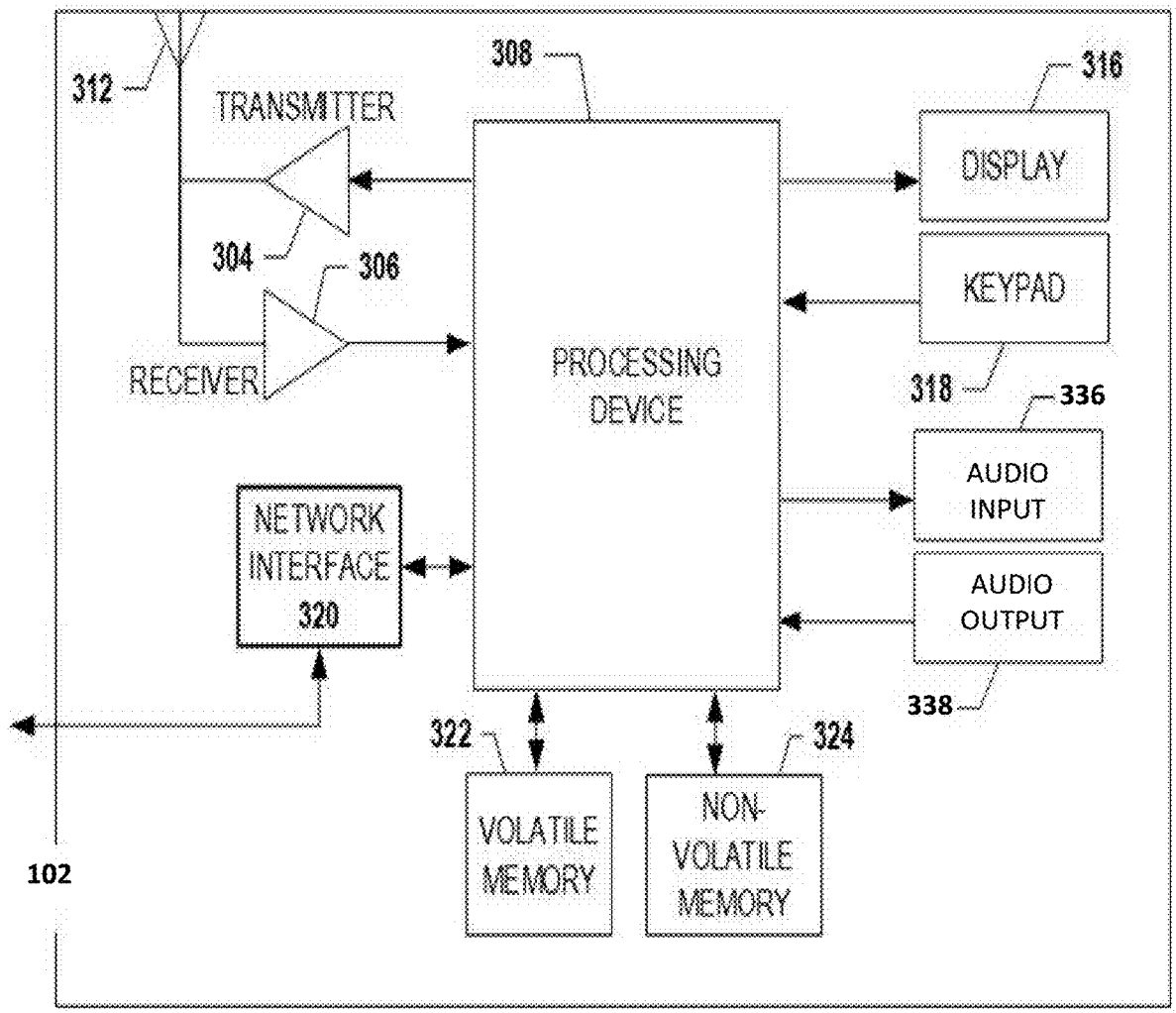

FIG. 3 illustrates an example provider computing entity in accordance with some embodiments discussed herein.

Figure 4:
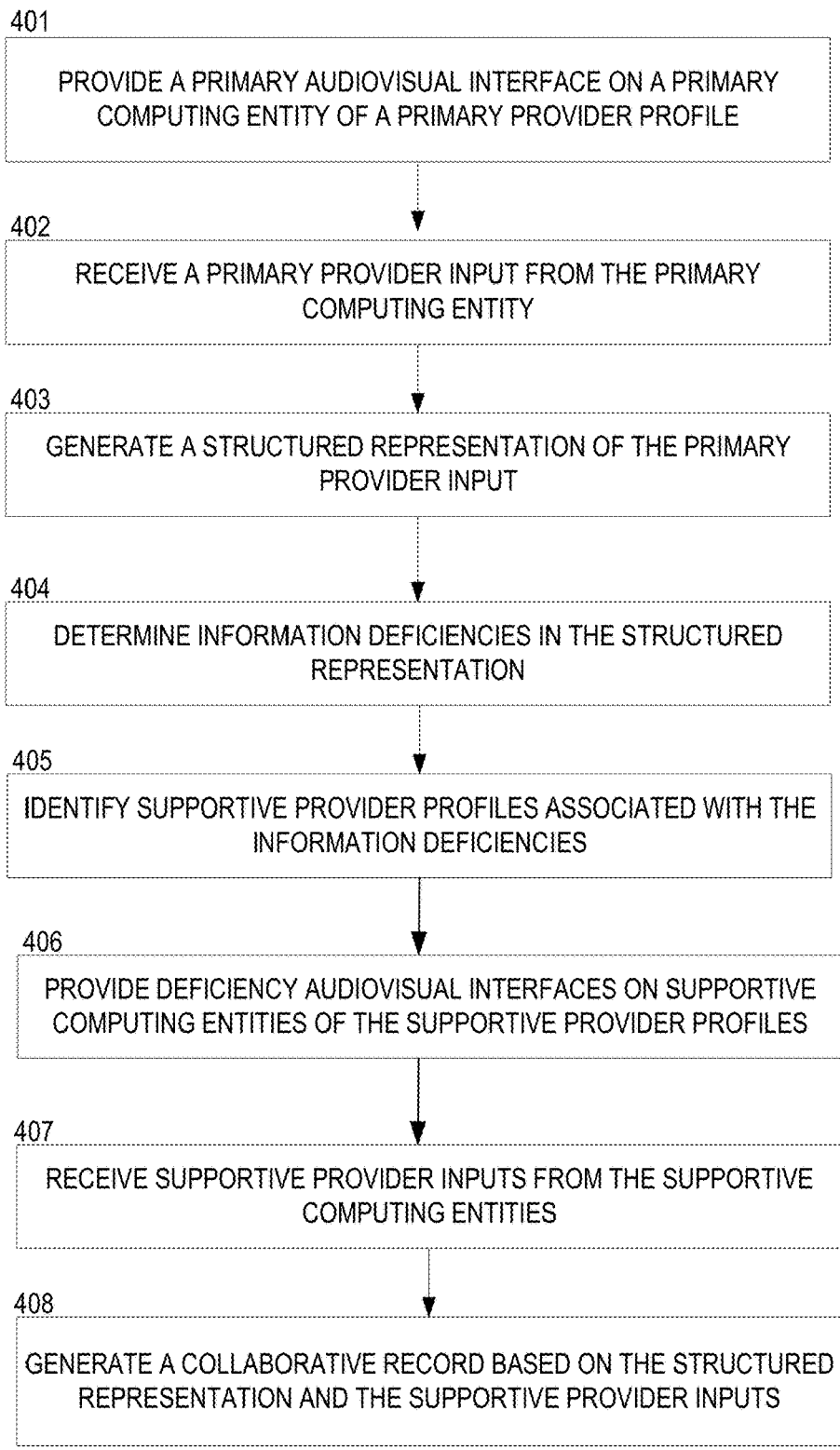

FIG. 4 illustrates a flow diagram of an example process for generating a collaborative medical service record.

Figure 5:
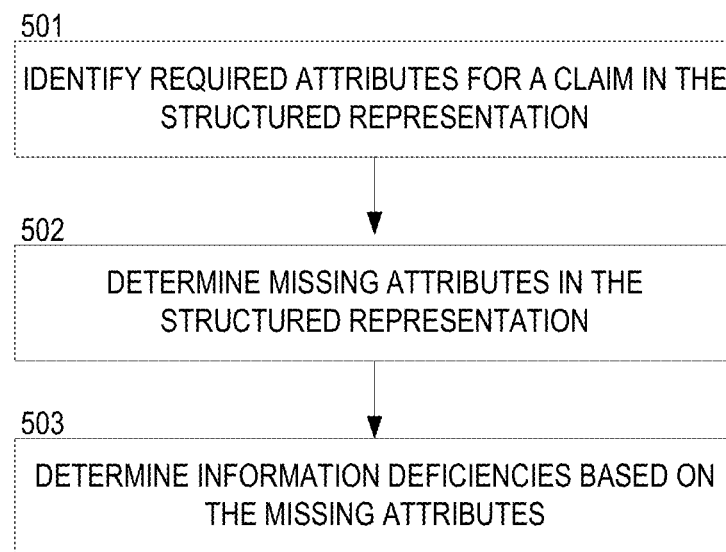

FIG. 5 illustrates a flow diagram of an example process for determining information deficiencies in the primary provider input.

Figure 6B:
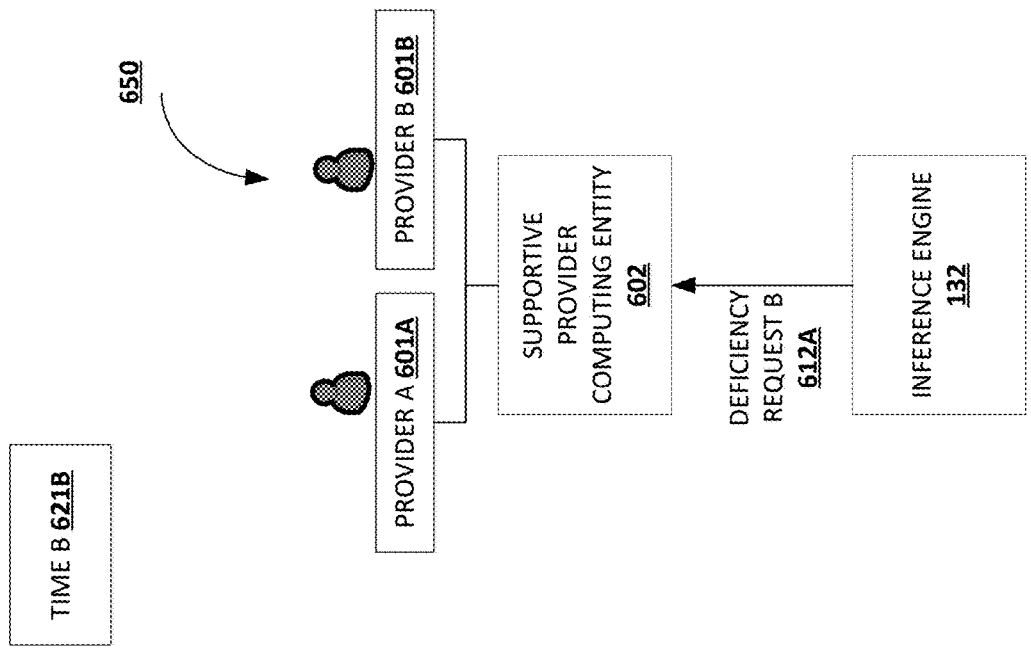
Figure 6A:
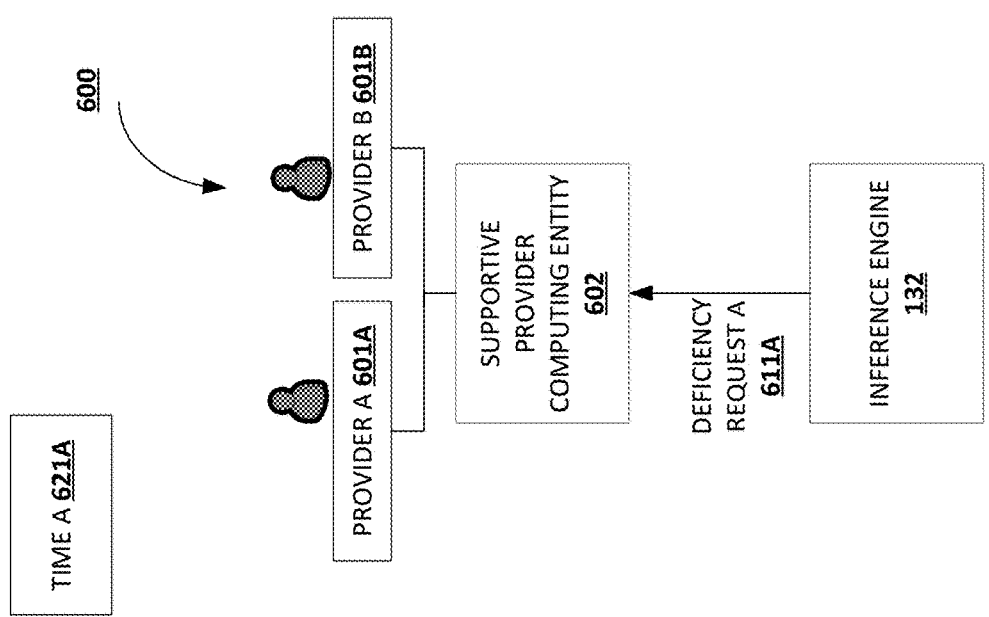

FIGS. 6A-6B depict operational examples of transmitting deficiency requests based on availability time.

Figure 7:
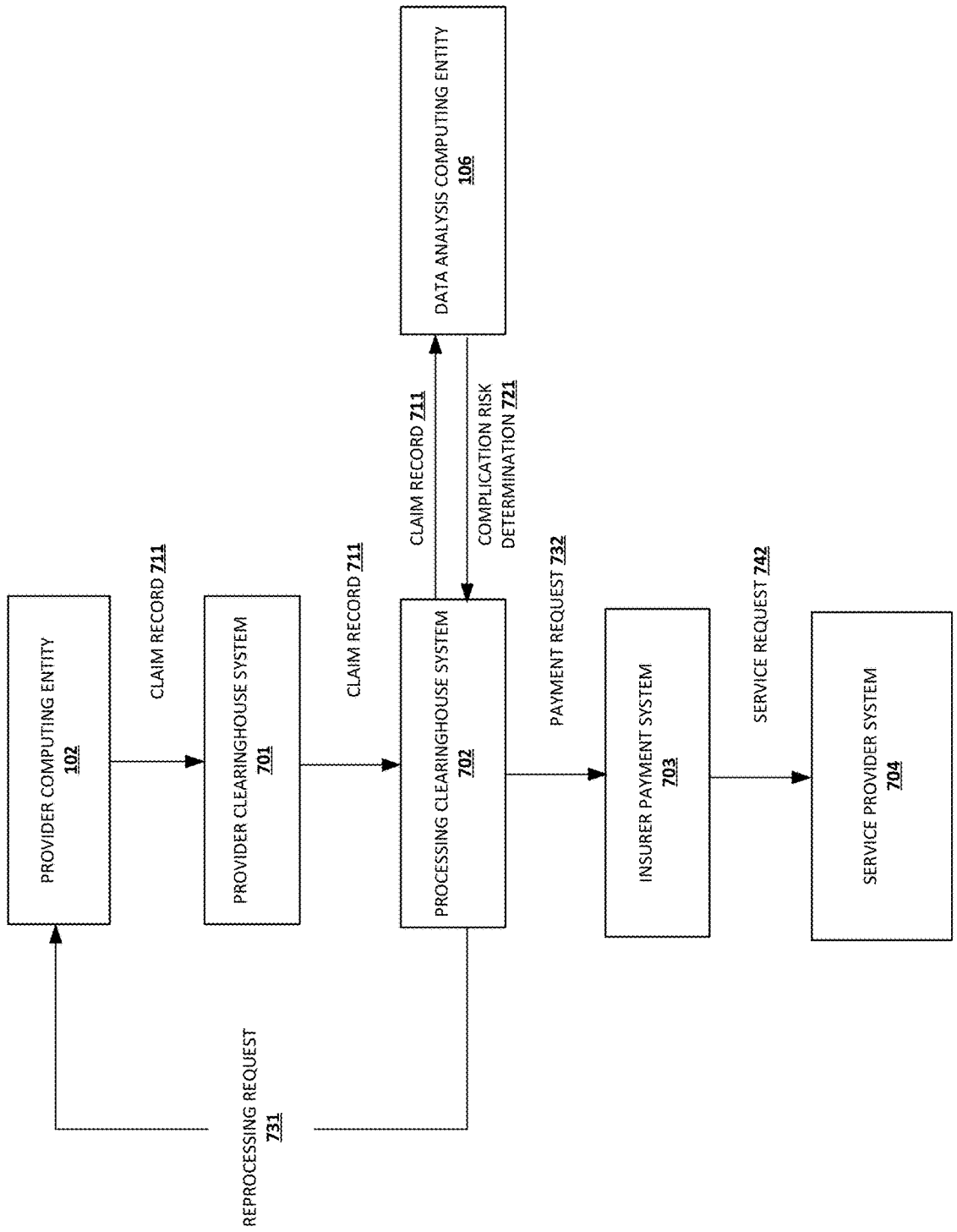

FIG. 7 illustrates a data flow diagram of an example process for processing a medical service claim based on a complication risk indication for the medical service claim.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

Moreover, while certain embodiments of the present invention are described with reference to monitoring memory loss, one of ordinary skill in the art will recognize that the disclosed concepts can be used to monitor other measures of cognitive capability in addition to or instead of memory loss.

I. Overview

Discussed herein are methods, apparatus, systems, computing devices, computing entities, and/or the like for collaborative generation of medical service reports, including features for automatically identifying appropriate information providers for various pieces of data to be included within a report. These systems may be further configured to generate user input requests to a plurality of computing devices associated with the identified information providers, thereby minimizing possible data entry delays resulting from more traditional methods of identifying various information providers. As will be recognized, however, the disclosed concepts can be used to generate other reports are not limited to a particular context. For example, various embodiments of the present invention may automatically identify appropriate information providers for various pieces of data by detecting information deficiencies in a primary provider input and identifying a supportive profile for each detected information deficiency. Moreover, various embodiments of the present invention may generate user input requests to identified information providers by causing each computing entity associated with an identified supportive profile to present an audiovisual interface that includes an indication of a query intended to obtain pieces of data related to the information deficiency associated with the identified supportive profile.

A. Technical Problems

Various embodiments of the present invention address the technological problem of automatically identifying collaborators who may have relevant information needed to complete a report (e.g., a medical service report, such as a billing report). Without such an automatic identification, medical record processing systems may need to rely on labor-intensive manual information collection from a primary author who may not have convenient access to all the information needed to complete a report and/or may not be aware of all the information needed to complete a report. For example, a medical service report may require information from administrative assistants, lab technicians, nurses, and physicians. If a medical record processing system tasked with generating such a report utilizes a single-source input mechanism, instead of a multi-party collaboration mechanism facilitated by automatic identification of desired information providers, such a medical record processing may fail to effectively and efficiently generate an optimal medical service report. This, in turn, undermines the efficiency and reliability of the medical record processing system.

Various embodiments of the present invention relate to the technological problem of addressing deficiencies in medical service reports (e.g., bills) in order to increase efficient and timely processing of such reports. Medical record processing systems that generate medical service records incur substantial inefficiencies resulting from incomplete and/or inaccurate data entry by providers. This is in part because the process of generating and processing medical service records includes a number of temporally sequential steps. Thus, a mistake at one step can slow down or render impossible completion of a task of a future step. As a result, many existing medical record processing systems are highly inefficient and suffer from major performance and reliability issues resulting from their unintelligent user interaction frameworks and medical service claim processing environments.

For example, a typical process for generating and processing medical service records may involve, after a medical service delivery session: (i) recording of medical notes by the provider, a task that can take days to complete, especially when the notes are in audio recording and the audio recording is transcribed by hand; (ii) producing medical service reports using information contained in the electronic medical records, including transcribed clinical notes, a task that can also take days; (iii) transmitting the medical service reports in large batches to payers (e.g., insurers); and (iv) assessing claim eligibility by the payers, which can also take days. This example is illustrative of the temporally sequential steps involved in processing of medical service records, in which each future step depends on the work of a previous step. In such an environment, a mistake in one step can compromise the work of future steps and incur substantial problems for efficient processing of medical claims.

Relatedly, existing medical record processing systems also fail to provide a user experience that allows information providers the ability to more meaningfully interact with the information in medical record systems. For example, existing systems fail to provide intelligent interactions between information providers and medical systems that enhances the work of the information providers and allows them to utilize the depth of information stored in medical record systems about patients, service types, payer institutions, etc. As a result, many existing medical record processing systems suffer from important technological challenges related to diminished user experience and quality of user interaction.

B. Technical Solutions

Various embodiments of the present invention address the technical problem of automatically identifying collaborators who may have relevant information needed to complete a report by detecting information deficiencies in a primary provider input and identifying a supportive profile for each detected information deficiency. Moreover, various embodiments of the present invention utilize the identified collaborators to obtain information needed to generate a report by, for example, causing each computing entity associated with an identified supportive profile to present an audiovisual interface that includes an indication of a query intended to obtain pieces of data related to the information deficiency associated with the identified supportive profile. Through those operations, various embodiments of the present invention make important contributions to solving technical problems associated with the efficiency and reliability of medical record processing systems that result from lack of automatic identification of collaborators who may have relevant information needed to complete reports and/or from generating reports via a single-source input mechanism, instead of a multi-party collaboration facilitated by automatic identification of desired information providers. Therefore, various embodiments of the present invention address technical problems associated with identifying collaborators who may have relevant information needed to complete a report.

Various embodiments of the present invention address the technical problem of inefficiency and/or unreliability in medical record processing systems due to incomplete and/or inaccurate provider input data through a collaborative data collection system configured to detect suspected data entry inaccuracies and to query providers (both the provider inputting the notes and other relevant providers identified as being in the same groups as the note-inputting provider) to provide information before medical service records are finalized (e.g., in real-time, as a provider is inputting medical notes by voice). For example, various embodiments of the present invention process a primary provider input in real-time using data maintained in a knowledgebase about properties of medical claims to detect whether the provider input is inaccurate and/or incomplete. If the system determines that the provider input is inaccurate and/or incomplete, the system automatically identifies providers associated with any information deficiencies and communicates with them to correct information deficiencies. This communication may be in real-time or within a substantially short amount of time from the time of information deficiency detection, thus increasing the speed and efficiency of medical record processing by a medical record processing system.

Collaborative aspects of the present invention allow multiple providers, and not just a provider who enters medical notes and/or who has conducted a medical visit, to provide input to the medical device processing system. By allowing collaboration between multiple providers, various embodiments of the present invention increase the efficiency of such systems by potentially increasing a speed of collecting information required to generate medical service records. This is because some information may be unavailable to particular providers in a group such that generating an accurate and/or complete record would be impossible without receiving input from those other information providers.

Various embodiments of the present invention can receive audio input from providers using audio sensors on computing devices. By enabling audio input to a medical device processing system, various embodiments improve user friendliness of such systems as audio input is often easier for users to input compared to other types of input, such as text input. Thus, by enabling audio input to a medical device processing system, various embodiments of the present invention can be utilized to create more user-friendly medical record processing systems.

Various embodiments of the present invention improve the efficiency of medical record processing systems by determining a complication risk associated with a medical claim and preventing inclusion of the claim in a medical service record and/or payment of the claim until one or more conditions are satisfied to reduce the complication risk associated with the medical service claim. For example, a complication risk indication may indicate a likelihood that an insurance company would deny a claim and/or request additional information prior to approving the claim. This risk may be calculated using information about policies of the insurance company and historical data about past decisions of the insurance company. By determining complication risks, the system may take proactive actions that reduce and/or eliminate the likelihood of denial of the claim, which would undermine the efficiency of the medical record processing system for providers.

Various embodiments of the present invention improve efficiency and effectiveness of medical record processing systems by enabling bi-directional communications between the medical record processing systems and providers who supply information to create medical records (e.g., where the providers transmit communications, for example provider input for a medical record, to a medical record processing system and the medical record processing system also transmits communications, e.g., questions, such as voice questions generated using voice synthesis, to the providers). Moreover, various embodiments of the present invention improve efficiency and effectiveness of medical record processing systems by enabling multi-modal communications between medical record processing systems and providers who supply information to create medical records (e.g., using two or more of text input, speech input, visual input, etc.). For example, the medical record processing system may provide one or more of an auto-generated text message containing a question, an auto-generated audio question prompt, and an auto-generated visual representation of a question to the provider. As another example, the provider may respond to queries by the questions posed by the medical record processing system by one or more of text messages, audio messages, and/or video messages. By utilizing a combination of the bi-directional communication and the multi-modal communication functionalities, various embodiments of the present invention enable a multi-modal conversational environment for recursive information gathering from one or more providers in order to create medical records, where the recursive information gathering obtains inputs from the providers across input segments (e.g., messages) and/or across conversational periods (e.g., chat sessions) to create effective and complete medical records.

Various embodiments of the present invention improve efficiency and effectiveness of a medical record processing system by intelligently determining deficiencies in provider input based on an inferred state of a knowledgebase associated with the medical record processing system and rules for deficiency determination based on the inferred state. For example, intelligent determination of a knowledgebase may include inferring conclusions from a structured representation of various data items stored in the knowledgebase, such as data items related to contacts, medical protocols, business processes, etc. In some embodiments, the medical record processing system may maintain a structured representation of a knowledgebase state that is updated over time (e.g., in real-time and/or using real-time data processing) to facilitate efficient and effective knowledgebase state inference and deficiency determination. The intelligent deficiency determination functionalities (e.g., including the intelligent knowledgebase state inference) can, in various embodiments, contribute to the advantages provided by the multi-modal conversational functionalities in order facilitate effective and efficient information gathering, e.g., effective and efficient information gathering in a recursive manner as described above.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1 illustrates an example system architecture 100 within which embodiments of the present invention may operate. A provider 101 may interact with a medical record processing system 105 via a provider computing entity 102. The provider computing entity 102 connects to the medical record processing system 105 via a communications network 103. The medical record processing system 105 includes a data analysis computing entity 106 and a knowledgebase 108, and interacts with one or more external computing entities 109. Each computing entity in the architecture 100 (e.g., the provider computing entity 102 and the data analysis computing entity 106) can include one computing device or multiple computing devices connected through one or more communications networks. Accordingly, each computing entity in the architecture 100 may include any suitable network server and/or other type of processing device.

For example, the provider computing entity 102 may be a computing entity that the provider 102 uses to provide data including medical notes (e.g., audio data including medical notes) as an input to the medical record processing system 105. The medical record processing system 105 may process the input from the provider computing entity 102 to generate a medical service report (e.g., a medical bill) to provide to external computing entities 109 (e.g., computing entities associated with payers for medical services, such as insurance companies). The medical record processing system may also receive data from the external computing entities 109. For example, the medical record processing system 105 may be configured to receive information about past reimbursement rates for various types of medical claims from external computing entities 109 associated with a health insurance company. The provider computing entity 102 may include a smartphone computing device, a tablet computing device, and/or a voice-assisted personal assistant computing device (such as an Amazon Echo, Amazon Echo Dot, Amazon Show, Google Home, etc.).

The communication network 103 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communication network 103 may include a cellular telephone, an 902.11, 902.16, 902.20, and/or WiMax network. Further, the communication network 103 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication system. In one embodiment, the protocol is a custom protocol of JSON objects sent via a Websocket channel. In one embodiment, the protocol is JSON over RPC, JSON over REST/HTTP, and the like.

The provider computing entity 102 is configured to present user interfaces, such as audiovisual interfaces, to the provider 101 based on information received from the medical record processing system 105 via the communication network 103. The provider computing entity 102 is further configured to receive provider 101 inputs, such as provider 101 inputs received using mouse, keyboard, touch, and/or audio input, and process the provider 101 inputs to generate information to provide to the medical record processing system 105 via the communication network 103.

The provider computing entity 102 includes an audiovisual interface provider 111, an input/output interface 112, a session data store 113 storing session data, a preference data store 115 storing preference data, and a presentation logic data store 114 storing presentation logic data. The audiovisual interface provider 111 is configured to receive inputs from and/or provide outputs (e.g., audiovisual interfaces) to the provider 101. The input/output interface 112 is configured to receive information from and/or provide information to the provider computing entity 102.

The audiovisual interface provider 111 may generate an audiovisual interface based on the presentation logic data, the information received from the medical record processing system 105 using the input/output interface 112 (e.g., information about updates to the knowledgebase 108 of the medical record processing system 105 and/or information about determinations by the data analysis computing entity 106 of the medical record processing system 105), the session data, and/or the preference data. The audiovisual interface may be part of a current user (e.g., provider 101) activity session, e.g., a current user activity session defined by a period of continued interaction by the provider 101 with the provider computing entity 102. The audiovisual interface may include audio elements only, visual elements only, or both audio elements and visual elements.

The session data includes data (e.g., structured data) about one or more properties of the current user activity session of the provider computing entity 102. The preference data includes data about one or more user preferences related to how to present audiovisual interfaces (e.g., data indicating user preferences related to presentation volume, presentation audio calibration, presentation font size, hotkey designation in a presentation, etc.). The presentation logic data include instructions configured to cause the audiovisual interface provider 111 to generate audiovisual interfaces in accordance with at least one of the information received from the medical record processing system 105, session data, and preference data. For example, the presentation logic data may include one or more of: (i) instructions configured to present visual elements generated by processing at least some of the session data and/or at least some of the information received from the medical processing system 105 using one or more visual presentation layouts; and (ii) instructions configured to present audio elements generated by processing at least some of the session data and/or at least some of the information received from the medical processing system 105 using one or more speech synthesis modules.

The audiovisual interface provider 111 may further receive provider 101 inputs and process the received provider 101 inputs to update the session data stored in the session data store 113, update the preference data stored in the preference data store 114, and/or cause the input/output interface 112 to provide information to the medical processing system 105 via the communication network 103. The input/output interface 112 may receive information from the medical record processing system 105 and process the received information to provide updates (e.g., interrupting updates and/or event handling updates) to the audiovisual interface provider 111 and/or the session data stored in the session data store 113.

The medical record processing system 105 is configured to receive input data from the provider computing entity 102 and process the input data to generate medical service reports. The medical record processing system 105 includes the data analysis computing entity 106 and the knowledgebase 108. The data analysis computing entity 106 includes a multi-modal transformation engine 131 and an inference engine 132.

The multi-modal transformation engine 131 may receive input data (e.g., input data including medical notes) from the provider computing entity 102. The multi-modal transformation engine 131 may process the input data to generate a structured representation of the input data to provide to the inference engine 132. For example, the multi-modal transformation engine 131 may perform one or more of the following: (i) convert input data having an audio format into a text format; and (ii) perform natural language processing on natural language data (e.g., natural language text data) to generate a structured representation of the natural language data).

The inference engine 132 may process (e.g., using a machine learning module with one or more trainable parameters) the structured representation of the input data received from the multi-modal transformation engine 132 to generate a medical service report. The inference engine 132 may provide a generated medical service report in the knowledgebase 108 and/or transmit the generated medical service report to an external computing entity 109. The inference engine 132 may, in addition to the structured representation of the input data received from the multi-modal transformation engine 132, use information stored in the knowledgebase 108 to generate medical service reports.

For example, the inference engine 132 may process the structured representation of the input data to identify one or more medical service claims (where a service claim may be a unit of service). The inference engine 132 may further identify one or more claim attributes associated with each medical service claim from the information in the input data and/or from the information stored in the knowledgebase 108. The inference engine 132 may further retrieve from the knowledgebase 108 informational requirements data for each identified medical service item, i.e., data indicating one or more claim attributes that the inference engine 132 should identify for each medical service claim before including the medical service claim in a medical service report. The inference engine 132 may compare the identified attributes for a medical service claim and the required attributes for the identified medical service claim to determine if the identified medical service claim is missing one or more required attributes. If the inference engine 132 determines that an identified medical service claim is missing one or more required attributes, the inference engine 132 may transmit information to one or more supportive computing entities (e.g., provider computing entity 102) that causes the one or more supportive computing entities to present audiovisual interfaces each requesting that a supportive provider (e.g., provider 101) provides at least one of the missing one or more required attributes.

The knowledgebase 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. In various embodiments, the knowledgebase 108 may include one or more of: (i) informational requirements data for medical service claims; (ii) data indicating attributes of medical service claims; (iii) data indicating at least some of past inputs to the medical record processing system 105; (iv) data indicating at least some previously-generated medical service reports; and/or (v) data used to train at least one component of the medical record processing system 105. In various embodiments, the knowledgebase 108 is configured to store data as one or more databases, such as one or more relational databases, and/or as one or more files having preconfigured formats, such as one or more files having a JSON format and/or one or more files having a format corresponding to a specialized graph database framework (e.g., a triplestore format and/or an Extensible Markup Language (XML) format).

The knowledgebase 108 may receive at least some of the data it stores from the data analysis computing entity 106, the provider computing entity 102, and/or at least one external computing entity 109. For example, the knowledgebase may receive informational requirements data from one or more external computing entities 109, such as external computing entities associated with medical payer institutions. As another example, the knowledgebase 108 may receive data indicating past inputs to the medical record processing system from the provider computing entity 109. As a further example, the knowledgebase 108 may receive data indicating previously-generated medical service reports from the inference engine 132 of the data analysis computing entity 106. As yet another example, the knowledgebase 108 may receive at least some data used to train at least one component of the medical record processing system 105 from one or more external computing entities 108. As an additional example, the knowledgebase 108 may store data indicating past inputs to the medical record processing system as training inputs and data indicating previously-generated medical service reports as training outputs.

A. Exemplary Data Analysis Computing Entity

FIG. 2 provides a schematic of a data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, radio frequency identification (RFID) tags, ear pieces, scanners, televisions, dongles, cameras, wristbands, wearable items, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the data analysis computing entity 106 may include or be in communication with one or more processing elements 205 (also referred to as processors, processing circuitry, and/or similar terms used herein interchangeably) that communicate with other elements within the data analysis computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the data analysis computing entity 106 with the assistance of the processing element 205 and operating system.

As indicated, in one embodiment, the data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR)

protocols, near field communication (NFC) protocols, Wibree, Bluetooth protocols, wireless universal serial bus (USB) protocols, and/or any other wireless protocol.

Although not shown, the data analysis computing entity 106 may include or be in communication with one or more input elements, such as a keyboard input, a mouse input, a touch screen/display input, motion input, movement input, audio input, pointing device input, joystick input, keypad input, and/or the like. The data analysis computing entity 106 may also include or be in communication with one or more output elements (not shown), such as audio output, video output, screen/display output, motion output, movement output, and/or the like.

As will be appreciated, one or more of the data analysis computing entity's 106 components may be located remotely from other data analysis computing entity 106 components, such as in a distributed system. Furthermore, one or more of the components may be combined and additional components performing functions described herein may be included in the data analysis computing entity 106. Thus, the data analysis computing entity 106 can be adapted to accommodate a variety of needs and circumstances. As will be recognized, these architectures and descriptions are provided for exemplary purposes only and are not limiting to the various embodiments.

B. Exemplary Provider Computing Entity

As discussed herein, a provider 101 is an information provider who inputs various data to be utilized by a medical records processing system 105 for the generation of a report. Thus, a provider 101 may be a medical care provider (e.g., a physician, a nurse, a physician's assistant, a medical assistant, and/or the like), an administrative assistant, a records technician, a medical billing coder, and/or the like. A provider 101 may be an individual, a representative of an organization and/or person, and/or the like. A provider 101 may operate a provider computing entity 102 that includes one or more components that are functionally similar to those of the management computing entity 101. FIG. 3 provides an illustrative schematic representative of a provider computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, RFID tags, ear pieces, scanners, televisions, dongles, cameras, wristbands, wearable items, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Provider computing entities can be operated by various parties. As shown in FIG. 3, the provider computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the provider computing entity 102 may be capable of operating with one or more air interface standards, communication protocols, modulation types, and access types. More particularly, the provider computing entity 102 may operate in accordance with any of a number of wireless communication standards and protocols, such as those described above with regard to the management computing entity 101. In a particular embodiment, the provider computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the provider computing entity 102 may operate in accordance with multiple wired communication standards and protocols, such as those described above with regard to the management computing entity 101 via a network interface 320.

Via these communication standards and protocols, the provider computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The provider computing entity 102 can also download changes, add-ons, and updates, for instance, to its firmware, software (e.g., including executable instructions, applications, program modules), and operating system.

According to one embodiment, the provider computing entity 102 may include location determining aspects, devices, modules, functionalities, and/or similar words used herein interchangeably. For example, the provider computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information can be determined by triangulating the provider computing entity's 102 position in connection with a variety of other systems, including cellular towers, Wi-Fi access points, and/or the like. Similarly, the provider computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The provider computing entity 102 may also comprise a user interface, such as audiovisual interface (that can include a display 316 coupled to a processing element 308 and/or an audio transmitter) and/or a user input interface (coupled to a processing element 308). For example, the user interface may be a user application, browser, user interface, and/or similar words used herein interchangeably executing on and/or accessible via the provider computing entity 102 to interact with and/or cause display of information from the management computing entity 101, as described herein. The user input interface can comprise any of a number of devices or interfaces allowing the provider computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the provider computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The provider computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the provider computing entity 102. As indicated, this may include a user application that is resident on the entity or accessible through a browser or other user interface for communicating with the management computing entity 101 and/or various other computing entities.

In another embodiment, the provider computing entity 102 may include one or more components or functionality that are the same or similar to those of the management computing entity 101, as described in greater detail above. As will be recognized, these architectures and descriptions are provided for exemplary purposes only and are not limiting to the various embodiments.

In various embodiments, a provider computing entity 102 may be embodied as an artificial intelligence (AI) computing entity, such as an Amazon Echo, Amazon Echo Dot, Amazon Show, Google Home, and/or the like. Accordingly, the provider computing entity 102 may be configured to provide and/or receive information/data from a user via an input/output mechanism, such as a display, a camera, a speaker, a voice-activated input, and/or the like.

In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event. For example, the AI computing entity may be configured to retrieve and/or execute a particular program (e.g., the described cognitive evaluation game) in response to an audible, vocal request from a user (e.g., a user speaking an instruction to the AI computing entity to execute the particular program).

IV. Exemplary System Operation

The operation of various embodiments of the present invention will now be described. As discussed herein, various embodiments are directed to systems and methods for collaborative generation of medical service records and other data reports by, e.g., automatically identifying appropriate information providers for various pieces of data to be included within a report and generating user input requests to a plurality of computing devices associated with the identified information providers. Through implementing the operations discussed herein, various embodiments of the present invention address the technical problems associated with automatically identifying collaborators who may have relevant information needed to complete a report and the technical problems associated with inefficiency and/or unreliability in medical record processing systems due to incomplete and/or inaccurate provider input data.

A. Generating Collaborative Medical Service Records

FIG. 4 is a flow diagram of an example process for generating a collaborative medical service record. The various steps of FIG. 4 enable systems and methods for collaborative generation of medical service records using data from multiple providers. In some embodiments, the systems and methods described herein enable real-time verification of sufficiency of medical notes, real-time collaborative aggregation of data from multiple providers and provider computing devices 102 corresponding those multiple providers to supplement deficient medical notes, and efficient generation of medical service records.

As indicated in block 401, the provider computing entity 102 provides a primary audiovisual interface on a primary computing entity associated with a primary provider profile. For example, the primary audiovisual interface provider 111 of the provider computing entity 102 may generate the primary audiovisual interface using instructions in the presentation logic data store 114 and one or more of the preference data stored in the preference data store 115 of the provider computing entity 102, the session data in the session data store 113 of the provider computing entity 102, and data received from the medical record processing system 105 using the input/output interface 112 of the provider computing entity 102. The primary audiovisual interface provider 111 may then present the generated audiovisual interface to the provider 111.

In some embodiments, the provider computing entity 102 may present an audiovisual interface in response to detecting an action by the provider 101, e.g., the clicking of a particular icon by the provider 101, the pressing of a button by the provider 101, and/or the declaration of a preconfigured phrase by the provider 101. In other embodiments, the provider computing 102 may generate the primary audiovisual interface without user action. For example, the primary computing entity 102 may present an audiovisual interface periodically and/or in response to one or more notifications received from other computing entities, e.g., a computing entity in the medical record processing system 105. In some embodiments, the medical record processing system 105 may transmit one or more notifications to the provider computing entity 102 indicating that a medical service appointment is predicted (e.g., based on a schedule) to be over at a particular time and cause the provider computing entity 102 to generate and present an audiovisual interface at the particular time.

The primary audiovisual interface may include audio elements only, visual elements only, or both audio elements and visual elements. For example, the provider computing entity 102 may emit an audio signal (e.g., a predefined audio signal and/or an audio signal generated using a speech synthesis transformation of data utilizing speech synthesis technology) that indicates that the provider 101 may provide input to the provider computing entity 102 through speaking. As another example, the provider computing entity 102 may display a graphical user interface (e.g., a graphical user interface generated using one more layouts for generating graphical user interfaces using input data) that allows the provider 101 to provide input to the provider computing 101 using one or more input methods, e.g., using a keyboard, using voice, etc. In some embodiments, the primary computing entity 102 is configured to receive an audio input and the primary audiovisual interface indicates that the provider 101 should provide input in audio format.

The primary audiovisual interface may be presented by a particular application on the primary computing device, where the operating system of the primary computing device may define one or more privileges for the particular application. For example, in some embodiments, the operating system may permit the particular application to present the primary audiovisual interface in response to one or more user actions configured to define a presenting mode for the particular application, e.g., one or more user applications intended to "open" the primary application or to switch to the user interface for the primary application. As another example, in some embodiments, the operating system of the primary computing entity may permit the particular application to present notifications to the user of the primary computing interface even when the particular application is not in the presenting mode, e.g., is in a background mode. In some embodiments, the operating system may permit the particular application to act as a driver application capable of sending interrupts to a processor of the primary computing entity.

In some embodiments, the primary audiovisual interface may include an interface element that depicts a representation of input by the provider 101. For example, the primary audiovisual interface may include a box that depicts a textual representation of audio input by the provider 101. In some embodiments, the primary audiovisual interface may include an interface element that provides one or more inquiries to the provider 101. For example, during a user activity session in which the provider 101 is providing medical notes to the provider computing entity 102, the provider computing entity 102 may detect (e.g., using notifications from the medical record processing system 105) that the provider 101 should provide particular information related to a subject of the medical notes (e.g., the blood pressure of an anemia patient). The primary computing entity 102 may present information in an interface element that reminds the provider 101 to provide the particular information.

At block 402, the medical record processing system 105 receives a primary provider input from a primary provider computing entity. For example, the multi-modal transformation engine 131 may receive the primary provider input from an input/output interface 112 of the provider computing entity, which in turn receives the primary provider input from the audiovisual interface provider 111 of the provider computing entity 102. The primary provider input is associated with the primary provider profile, which is in turn associated with the primary computing entity 102. In some embodiments, the primary provider input includes an audio component. In some embodiments, the primary provider input includes one or more of at least one audio input component, at least one text input component, at least one scanned image component, etc.

In some embodiments, the primary provider input is associated with one or more segment identifiers, at least one of which indicates a type or category of at least a segment of the primary provider input. For example, the primary provider input may include a first segment with data indicating health insurance information of a patient, a second segment with data indicating lab results associated with the patient, a third segment with data indicating a medical diagnosis for a condition of the patient, and a fourth segment with data indicating medications prescribed for the condition of the patient. An information provider may provide one or more segments of the data in the primary provider input, and input provided within each segment may be provided in free-form, such that each segment may comprise a plurality of discrete data elements included in an unstructured format. For example, an administrative information provider may provide the first segment described above (e.g., in a conversational interaction with a computing device), a lab technician information provider may provide the second segment (e.g., in a conversational interaction with a computing device in which various lab-related data points are provided in a single continuous user input (e.g., a single speech input provided by the provider), and a medical professional information provider may provide the third and fourth segments. In some embodiments, the primary provider input includes the one or more segment identifiers described above when received by the medical record processing system 105. For example, the input/output interface 112 may generate the segment identifiers and include them as part of the primary provider input. In some embodiments, the medical record processing system 105 preprocesses the primary provider input to generate the one or more segment identifiers and/or to extract relevant data within free-form input provided for a particular segment.

To generate the one or more segment identifiers associated with the primary provider input, a component of the architecture (e.g., the input/output interface 112 and/or the multi-modal transformation engine 131) may process an indication of an information provider that is a source of a portion of the primary provider input and/or one or more actions by the information provider, e.g., one or more actions by the information provider associated with inputting the portion of the primary provider input. For example, the component may determine that a first portion of the primary provider input is from a lab technician information provider, and thus determine based on that information that the first portion has a lab result type or category. As another example, the component may determine that a second portion of the primary provider input has been entered by a medical professional information provider after clicking a button associated with entering medical diagnosis data and/or in a user interface element associated with entering medical diagnosis data, and thus determine based on that information that the second portion has a medical diagnosis type or category. In some embodiments, the component may determine type or category of a segment of the primary provider input based on the contents of the segment, e.g., using one or more natural language processing modules.

In some embodiments, the input/output interface 112 may perform one or more transformations on the primary provider input prior to transmitting the primary provider input to the multi-modal transformation engine 131. For example, the input/output interface 112 may process an audio input to remove segments and/or portions determined to include background noise. In some embodiments, the input/output interface 112 compresses the primary provider input prior to transmitting the primary provider input to the multi-modal transformation engine 131. For example, the input/output interface 112 may compress audio data that includes a representation of audio input by the provider 101. The input/output interface 112 may perform the compression using at least one lossy compression algorithm and/or at least one lossless compression algorithm. In some embodiments, the input/output algorithm 112 may compress different segments and/or portions of primary provider input using different compression algorithms. For example, the input/output algorithm may determine that a first segment of the primary provider input is likely to be less important (e.g., contain no or little provider 111 voice data) and compress the first segment using a lossy algorithm having a higher compression ratio. In addition, the input/output algorithm may determine that a second segment of the primary provider input is likely to be more important (e.g., contain sufficient provider 111 voice data) and compress the first segment using a lossless algorithm having a lower compression ratio.

At block 403, the medical record processing system 105 (e.g., using the multi-modal transformation engine 131) processes the primary provider input to generate a structured representation of the primary provider input (e.g., a collection of one or more discrete data elements from the primary provider input). In some embodiments, the structured representation has a format corresponding to an expected input of the inference engine 132 of the data analysis computing entity 106 of the medical record processing system 105. For example, if the inference engine 132 is a machine learning module that receives a vector of n input values, the structured representation may also be a vector of n input values, where some of the input values in the vector may be undefined values if the multi-modal transformation engine 131 fails to detect those particular values. Moreover, each of the input values may comprise a data object comprising text (e.g., transcribed from a voice-memo), an audio-file, and/or the like.

In some embodiments, the multi-modal transformation engine 131 performs one or more transformations on the primary provider input. For example, the multi-modal transformation engine 131 may decompress the primary provider input, remove background noise from the primary provider input, convert format of a non-textual component (e.g., an audio component) of the primary provider input into a text format, and/or determines one or more attribute of at least one medical service claim from the primary provider input. For example, the multi-modal transformation engine 131 may, before or after one or more other transformations, perform natural language processing on the primary provider input to determine one or more medical service claims as well as one or more attributes of at least one medicals service claim from the primary provider input. The multi-modal transformation engine 131 may then use the determined medical service claims and corresponding attributes to generate a structured representation of the primary provider input.

For example, the multi-modal transformation engine 131 may receive, as primary provider input, a compressed audio file, decompress the compressed audio file to generate a decompressed audio file, detect (e.g., using a machine learning module) background noise in the decompressed audio file, remove the detected background noise (e.g., utilizing a filter module, operating as a high-pass filter, a low-pass filter, a band-pass filter, and/or the like. For example, the filter module may be configured to filter out noises falling within a given frequency range (e.g., within a defined range centered on 60 Hz), noises falling below a given volume, and/or the like) from the decompressed audio file to generate a refined audio file, and convert the refined audio file to corresponding text data, for example, via an automated transcription module. If, for example, the corresponding text data associated with the primary provider input includes the text segment "after reviewing the MRIs, the patient appears to suffer from a category I shoulder dislocation," the multi-modal transformation engine 131 may determine that the primary provider input is associated with a medical service claim related to MRI review and determine that the identified medical service claim is associated with attributes related to the particular bodily organ subject to medical imaging (i.e., shoulder) and the particular diagnosed condition (i.e., category I shoulder dislocation). The multi-modal transformation engine 131 may then use the determined medical service claim and corresponding attributes to generate a structured representation of the primary provider input.

In some embodiments, the structured representation is a hierarchical data structure that designates one or more general attributes for the primary provider input (e.g., a patient identifier, medical provider identifier, etc.), one or more service identification attributes each identifying a service claim described in the primary provider input, and, as sub-attributes of each service identification attribute identifying a particular service claim, one or more service property attributes each identifying a property of the particular service claim. The structured representation may include, as a sub-attribute of a service identification attribute identifying a particular service claim, a complication risk indication associated with the service claim. In some embodiments, the multi-modal transformation engine 131 may determine one or more attributes of the structured representation by analyzing properties associated with the primary provider input and/or by analyzing contents of the primary provider input, e.g., using a natural language processing module.

At block 404, the medical record processing system 105 (e.g., using the inference engine 132) detects the one or more information deficiencies in the primary provider input. An information deficiency is an indication of a missing required attribute and/or a missing optimal attribute in the primary provider input, i.e., an attribute of a medical service claim that should be provided before inclusion of the claim in a medical service report but that has not been determined by the primary provider input. In some embodiments, the medical record processing system 105 detects the one or more information deficiencies using the informational requirements data. A discussion of specific processes for identifying information deficiencies is included in subsection B.

In some embodiments, the medical record processing system 105 may first use one or more lower-order attributes of the primary provider input to determine a lower-order type of the primary provider input. For example, the medical record processing system 105 may use one or more of at least a portion of content of the primary provider input, a provider identifier associated with the primary provider input, and a patient identifier associated with a primary provider input to determine a lower-order type of the primary provider input indicating that the primary provider input relates to a medical record for a surgery. The medical record processing system 105 may then use the lower-order type of the primary input to retrieve a required model for the lower-order type, where a required model for a particular lower-order type may define a model defining one or more required attributes for each primary provider input having a particular lower-order type. For example, the medical record processing system 105 may retrieve a required model for a surgery-related lower-order type that indicates that a surgery-related primary provider input must include an indication of a type of the surgery. The medical record processing system 105 may then use the required model for a lower-order type of a primary provider input and a structured representation of the primary provider input to determine missing required attributes in the primary provider input. For example, if a required model for a primary model requires presence of required attributes A-C while structured representation of the primary provider input includes attributes A and B, the medical record processing system 105 may determine that the primary provider input needs values for the missing required attribute C. Moreover, the medical record processing system 105 may use values for at least some of the required attributes for a primary provider input to determine a higher-order type of the primary provider input and determine an optimal model for the higher-order type, where the optimal model for a particular higher-order type may define one or more optimal attributes for each primary provider input having the particular higher-order type. For example, the medical record processing system 105 may use a value denoting that a surgery-related primary provider input relates to a tumor removal surgery to retrieve an optimal model for the tumor removal surgery that defines an optimal attribute related to the benignness of the tumor. The medical record processing system 105 may then use the optimal model for a higher-order type of a primary provider input and a structured representation of the primary provider input to determine missing optimal attributes in the primary provider input. For example, if an optimal model for a primary model requires presence of required attributes D-F while structured representation of the primary provider input includes attributes D and E, the medical record processing system 105 may determine that the primary provider input needs values for the missing optimal attribute F.

Each information deficiency may be associated with a query, i.e., a request to provide one or more information items related to an attribute of a medical service claim. For example, if a claim for a medical examination of an anemia patient is missing a required attribute related to blood pressure of the patient, the inference engine 132 may determine an information deficiency related to the missing attribute. The determined information deficiency may be associated with a query for the missing attribute to lab technician provider and/or a query to a recordkeeping provider. Returning to FIG. 4, at block 405, the medical record processing system 100 (e.g., using the inference engine 132) identifies, for each information deficiency, one or more supportive profiles associated with the respective information deficiency. For example, the inference engine 132 may retrieve information from the knowledgebase 108 that identifies one or more supportive profiles for each information deficiency. The supportive profiles may each indicate a supportive provider profile (e.g., a profile of provider 101) that is deemed eligible and/or knowledgeable to provide information about the missing attributes related to the information deficiency. For example, the inference engine 132 may identify a lab provider as a supportive profile for an information deficiency related to a lab result. As another example, the inference engine 132 may identify an entire team relating to a primary provider as eligible supportive profiles that may each (collectively or in the alternative) provide additional needed information to remedy one or more information deficiencies.

The inference engine 132 may then transmit a deficiency request for each information deficiency (i.e., a request for providing information to correct the information deficiency) to the input/output interface 112 of the supportive provider computing entities associated with the information deficiency. The inference engine may transmit the deficiency request using one or more information packets transmitted over the communication network 103, where the one or more information packets may designate the missing attributes and/or the supportive provider profiles that relate to the information deficiency associated with the deficiency request. The inference engine 132 may transmit the deficiency request at a time after detection of a corresponding information deficiency and determination of supportive profiles associated with the information deficiency. In some embodiments, the inference engine 132 may transmit the deficiency request to each supportive profile based on the availability status and/or availability schedule of the supportive profiles at one or more times. In some embodiments, the inference engine 132 transmits the deficiency requests to one or more supportive profiles in order to enable real-time generation of a service record, i.e., generation of the service record within a substantially small time from the time of entry of a primary provider input that starts the record generation process.

In some embodiments, the inference engine 132 may determine that the primary provider profile is also a supportive provider profile. This may happen, for instance, when the architecture 100 operates to provide real-time feedback to the primary provider profile at a time sufficiently close to a time of receiving the primary provider input from the primary provider profile. In many cases, the provider associated with the provider profile that is providing the primary provider input (i.e., the primary provider profile) may indeed be in the best position to provide missing and/or additional attributes related to information deficiencies. In some embodiments, the inference engine 132 identifies at least one supportive provider profile which is different from the primary provider profile even during the real-time feedback scenario. This may be because the provider associated with the primary profile is not knowledgeable about the subject of the information deficiency and/or is not available to provide information about the information deficiency. In general, when an information deficiency relates to two or more candidate supportive provider profiles, the inference engine 132 may determine a cost of communicating with each candidate supportive profile to correct the information deficiency (e.g., based on one or more of an availability of the candidate supportive profile, a position of the candidate supportive profile, a billing rate of the candidate supportive profile, etc.), and identify the candidate supportive profile having the lowest cost as the supportive primary profile.

At block 406, the supportive provider computing entity 102 for each identified supportive profile presents a supportive audiovisual interface to the supportive profile computing entity of the supportive provider profile. For example, the audiovisual interface provider 111 for an identified supportive profile may generate the supportive audiovisual interface using instructions in the presentation logic data store 114 based on information items received by the input/output interface 112 of the supportive provider computing entity 102, e.g., based on the deficiency request.

Similar to a primary audiovisual interface, a supportive audiovisual interface may be invoked in different ways, may include different components of different types, and/or may include different interface elements depicting different information items. For example, the audiovisual interface provider 111 may provide audiovisual notifications that inform the supportive provider profile of an information deficiency and allow the supportive provider profile to select to input information related to the information deficiency. In some embodiments, a supportive audiovisual interface has an audio component (e.g., a predefined audio signal and/or an audio signal generated using speech synthesis). In some embodiments, a supportive audiovisual interface has a visual component (e.g., a visual component generated using one or more layouts for generating a graphical user interface).

The supportive audiovisual interface for an identified supportive provider profile may include an indication of the query associated with the information deficiency for the identified provider profile. The audiovisual interface provider 111 may include an indication of the query in one or more interface elements in a supportive audiovisual interface. The placement of the indication of query in particular interface elements may depend on a state of the supportive computing entity at time of receiving a deficiency request. For example, while the primary provider 101 is inputting the primary provider input, the primary provider computing entity 102 may present an audiovisual interface having a first interface element that presents inquiries to the primary provider. If the primary provider computing entity 102 receives a deficiency request related to an information deficiency in the primary provider input during this inputting state, the audiovisual interface provider 111 may include an indication of the query related to the information deficiency in the first interface element.

In certain embodiments, the supportive audiovisual interface may provide a conversational engagement with the identified provider associated with the supportive provider profile. For example, as additional information is provided by the identified provider (or by one of a plurality of identified providers), the provided data may be transmitted back to the multi-modal transformation engine 131 for processing by the inference engine 132 in real-time. If additional information is needed, the inference engine 132 may transmit a new query to the supportive provider's computing entity for presentation to the user thereof. This process may continue, with questions or other requests for information being provided to the supportive provider, and the supportive provider providing additional data in response.

In certain embodiments, if a supportive provider does not provide adequate information to remedy all information deficiencies, the inference engine 132 may identify another supportive provider to request additional information therefrom.

In some embodiments, the inference engine 132 may transmit deficiency requests based on one or more properties of a supportive provider profile associated with a deficiency request, such as an availability of the supportive provider profile. For example, the inference engine 132 may determine (e.g., based on a calendar and/or an availability status) that a particular supportive provider profile is only expected to be available at a particular supportive computer entity at a particular time. Accordingly, the inference engine 132 may transmit a deficiency request associated with the particular supportive provider profile to the particular supportive computing entity at the particular time. By transmitting deficiency requests at times best suitable for supportive provider collaboration, the techniques described in this specification can further facilitate collaborative generation of medical service records.

FIGS. 6A-6B depict operational examples of transmitting deficiency requests based on availability times of supportive provider profiles. The operational example 600 in FIG. 6A occurs at a time A 621A, which is a time when only supportive provider profile A 601A is available at the supportive computing entity 602. Thus, at the time A 621A, the inference engine 132 transmits deficiency request A 611A, a deficiency request intended for the supportive provider profile A 601A, to the supportive computing entity 602. In contrast, the operational example 650 in FIG. 6B occurs at a time B 621B, which is a time when only supportive provider profile B 601B is available at the supportive computing entity 602. Thus, at the time B 621B, the inference engine 132 transmits deficiency request B 611B, a deficiency request intended for the supportive provider profile B 601B, to the supportive computing entity 602.

Returning to FIG. 4, at block 407, the medical record processing system 105 (e.g., using the multi-modal transformation engine 131) receives a supportive provider input from the supportive profile computing entity associated with each identified supportive provider. In various embodiments, the audiovisual interface provider 111 of the supportive provider computing entity 102 for each identified supportive profile receives the supportive provider input from the identified supportive profile and provides the supportive provider input to the input/output interface 112 of the supportive provider computing entity 102. The input/output interface 112 may perform one or more transformations (e.g., compression, removing background noise, etc.) on the supportive provider input and transmit, via the communication network 103, the supportive provider input to multi-modal transformation engine 131. Like the primary provider input, a supportive provider input may have different components having different formats. For example, the supportive provider input may have an audio component having an audio and/or a textual component having a text format. In some embodiments, the supportive provider input includes an identifier of the supportive provider profile.

At block 408, the medical record processing system 105 generates a collaborative medical service record based on the structured representation of the primary provider input and each received supportive provider input. For example, the medical record processing system 105 may process each received supportive provider input to generate a structured representation of each supportive provider input. This process may be performed by the multi-modal transformation engine 131 in a manner similar to the manner described above with reference to block 403. In addition, the medical record processing system 105 may (e.g., using the inference engine 132) process the structured representation of the primary provider input and the structured representation of each received supportive provider input to generate a medical service record associated with one or more medical service claims.

Generating a medical service record may include determining if a combination of attributes provided by the primary provider input and each supportive provider input includes all the required attributes for a medical service claim. This process may be performed in a manner similar to the manner described with respect to block 403. If the medical record processing system 105 determines that a combination of attributes provided by the primary provider input and each supportive provider input includes all the required attributes for a medical service claim, the medical record processing system 105 will generate a medical service record that includes the medical service claim. However, if the medical record processing system 105 determines that a combination of attributes provided by the primary provider input and each supportive provider input does not include all the required attributes for a medical service claim, the medical record processing system may repeat steps similar to those described with respect to blocks 404-407 to obtain missing attributes, associated information deficiencies, associated supportive provider profiles, and/or associated supportive provider inputs.

In various embodiments, a process for generating medical service records as described herein (e.g., the process described in FIG. 4) may be performed at a time substantially close to a time of a first primary provider entry. For example, in various embodiments, the operations described with respect to blocks 401-408 may be performed at substantially close points in time and with minimal delay. This may result in a real-time verification of sufficiency of medical notes, real-time collaborative aggregation of data from multiple providers to supplement deficient medical notes, and efficient generation of medical service records.

B. Identifying Information Deficiencies in Information Provider Inputs

The inference engine 132 of the medical record processing system 105 may determine information deficiencies in the primary provider input using one or more deficiency detection methods, e.g., a combination of two or more deficiency detection methods, with a weight optionally applied to an output of each method. For example, one deficiency detection may detect an information deficiency when a complication risk indication associated with a service claim identified in the primary provider input indicates that the service claim is risky. An example of such a method is described in subsection C. Another deficiency detection method detects an information deficiency based on whether a structured representation of the primary provider input includes discrete data elements indicated in informational requirements data. An example of such a method is described herein.

The inference engine 132 may receive informational requirements data from the knowledgebase 108 and use the received informational requirements data to determine information deficiencies in the primary provider input. An example process for determining information deficiencies in the primary provider input based on informational requirements data is provided in FIG. 5. As indicated in block 501 of FIG. 5, the inference engine 132 may identify required attributes for a medical service claim using the informational requirements data stored in the knowledgebase 108. For example, the knowledgebase 108 may store informational requirements data determined based on one or more of medical guidelines, payer institution guidelines, past payer institution practices (e.g., rejection rates), etc. Such informational requirements data may indicate one or more requirement attributes for each medical service claim. For example, the informational requirements data may include that, medical services of a particular type should include particular attributes before inclusion in a medical service report. The particular type of a medical service claim may depend on patient condition, nature of service, timing of the delivery of the service, etc.

In some embodiments, the inference engine 132 determines the one or more required attributes for a medical service claim based on a complication risk indication for the medical service claim, i.e., a likelihood that the service claim faces a complicating condition in the future. For example the inference engine 132 may determine that a particular service claim has a high complication risk indication and, in response, require additional attributes and/or documentation to be supplied with the medical service claim. To determine the complication risk indication for a service claim, the inference engine 132 may perform one or more of the following: (i) query the knowledgebase 108 based on one or more attributes of the service claim to retrieve, as the result of the query, the complication risk indication for the service claim; and (ii) query the knowledgebase 108 for one or more complication risk indication rules and apply those rules to the service claim to determine the complication risk indication for the service claim. Once the inference engine 132 determines the complication risk indication for a service claim, the inference engine 132 may query the knowledgebase 108 for one or more required attributes for service claims having the particular complication risk indication.

As indicated in block 502 of FIG. 5, the inference engine 132 may determine missing attributes in the structured representation of the primary provider input. For example, the inference engine 132 may compare the attributes in the structured representation to the required attributes. To the extent the structured representation does not include a defined value for a required attribute, the inference engine 132 may classify the particular required attribute as a missing attribute. In some embodiments, the inference engine 132 may initially process (e.g., base the structured representation to infer new attributes from the structured representation (e.g., based on medical guidelines stored in the knowledgebase 108 and/or based on past primary provider inputs)) and generate a processed representation of the primary provider input. The inference engine 132 may then compare the attributes in the processed representation to the required attributes. To the extent the processed representation does not include a defined value for a required attribute, the inference engine 132 may classify the particular required attribute as a missing attribute.

As indicated in block 503 of FIG. 5, the inference engine 132 may determine information deficiencies in the primary provider input based on the missing attributes. In some embodiments, the inference engine 132 may determine an information deficiency corresponding to each determined missing attribute. In some embodiments, the inference engine 132 may determine (e.g., based on information in the knowledgebase 108) that two or more missing attributes are sufficiently related, and thus determine a single information deficiency corresponding to all of the two or more missing attributes.

In some embodiments, the inference engine 132 may determine the information deficiencies without using the informational requirements data. For example, the inference engine 132 may determine information deficiencies using an artificial intelligence module with one or more trained parameters. As another example, the inference engine 132 may determine information deficiencies using a rule-based module with one or more deficiency determination rules. The machine learning module may, for example, be a feedforward or recurrent neural network. The parameters of the machine learning module may be trained using input training data and output training data stored in the knowledgebase 108. For example, a training module may train the machine learning module using training data related to past medical service records and/or data from external computing entities 109 (e.g., data about past rejections by payer institutions). The training module may use a training algorithm such as gradient descent or gradient descent with backpropagation.

C. Complication Risk Management in Medical Claim Processing

Various embodiments of the present invention determine a complication risk indication for a medical service claim and request that a provider 101 reprocesses the medical service claim based on the complication determination. This process may occur after a medical service claim is finalized as discussed herein, or this process may occur as the claim is being generated. In some embodiments, in addition to or instead of determining one or more information deficiencies associated with a medical service claim, the medical record processing system 105 may determine that a medical service claim has a high complication risk, i.e., is likely to face a complication condition such as being denied and/or being deemed to include inaccurate and/or insufficient information. For example, the complication risk of a medical service claim may relate to (e.g., may describe) a likelihood that the medical service claim (e.g., in a current state) creates a gap in coverage (e.g., by failing to provide one or more appropriate service codes or other information for a medical service item such as a medical visit or a medical procedure). Such gaps in coverage may relate to information required/recommended for storage to ensure a patient's medical record is complete, for example. In response to determining that a medical service claim has a high complication risk, the medical record processing system 105 may request that the provider computing entity 102 reprocesses the medical service claim by, e.g., including additional information and/or verification documents along with the medical service claim to reduce complication risk indication associated with the medical service claim.

FIG. 7 provides a data flow diagram for an example process for processing a medical service claim based on a complication risk indication for the medical service claim. As depicted in FIG. 7, the provider computing entity 102 provides a claim record 711 to a provider clearinghouse system 701, which in turn transmits the claim record 711 to a processing clearinghouse system 702 (e.g., a payor clearinghouse system). The processing clearinghouse system 702 provides the claim record 711 to the data analysis computing entity 106, which computes a complication risk indication 721 for the claim record 711. The claim record 711 may be an indication of a service claim in a service record generated using a service record generation method, such as the method of FIG. 4, or an indication of a service claim generated using other methods.

In some embodiments, the data analysis computing entity 106 computes an overall complication score for the claim record 711 based on one or more attributes of the claim record 711 and determines the complication risk indication based on whether the complication score exceeds a threshold score. In some embodiments, determining the overall complication score for a claim record 711 may include identifying one or more attributes of a claim (e.g., service type of a claim, insurer identifier associated with a claim, etc.), determining an individual risk score associated with each identified attribute based on or more conditions (long descriptions, indications of medical necessity, etc.) associated with historical treatment (e.g., past approval of) claims having the same or similar attribute (e.g., using a mapping table associating each attribute with the one or more conditions); and determining the overall complication score for the claim record 711 based on the individual complication score of each identified attribute. For example, the data analysis computing entity 106 may determine that service claims related to a nose surgery operation have a history of not being covered by insurance plans in many cases and thus determine that a claim record 711 related to nose surgery has a high claim risk determination 721.

In some embodiments, the data analysis computing entity 106 generates a complication determination for a claim record 711 based on whether one or more attributes of the claim record 711 satisfy one or more complication rules (e.g., which may be stored in the knowledgebase 108). The data analysis computing entity may determine the complication risk indication 721 for the complication record 711 by processing the medical claim using the inference engine 132. The inference engine 132 may retrieve data used to identify one or more attributes of the claim record 711 and/or data associated with past approval of claims from the knowledgebase 108 and/or from at least one external computing entity 109.

In some embodiments, the data analysis computing entity 106 can infer a complication risk from the knowledgebase 108, e.g., using information such as eligibility, provider contracts, medical protocols, business processes, etc. In some embodiments, the data analysis computing entity 106 can determine a complication risk using a machine learning model trained (e.g., using historical data associated with the medical record processing system 105) to predict a complication risk for a medical service claim based on one or more attributes of the medical service claim (e.g., one or more of contents of the medical service claim, a patient identifier associated with the medical service claim, a provider identifier associated with the medical service claim, one or more service codes associated with the medical service claim, etc.). In some embodiments, the data analysis computing entity 106 may use a complication risk of a medical service claim and/or information used to determine the complication risk of the medical service claim to generate conclusions about health of a patient. For example, given that a medical service claim relates to a medical service concerning obesity, and given that the complication risk of the medical service claim indicates a high complication risk, the data analysis computing entity 106 may conclude that the patient may suffer from morbid obesity.

The data analysis computing entity 106 transmits the complication risk indication 721 to the processing clearinghouse system 702. If the processing clearinghouse system 702 determines based on the complication risk indication 721 that the claim record 711 is risky (i.e., likely to face a complicating condition, such as denial by a payer institution and/or an additional information request by a payer institution), the processing clearinghouse system 701 will transmit a reprocessing request 731 to the provider computing entity 731. The reprocessing request 731 may request additional information and/or verification documents to reduce a complication risk indication associated with the medical service claim. The nature and quantity of additional information and/or verification documents included in a reprocessing request 731 may depend on the determined risk of the claim record 711. For example, the reprocessing request 731 for a moderately risky claim record 711 may request additional information about a medical service subject to the request, while a highly risky claim record 711 may request documentation verifying details of services. The reprocessing request 731 may also include a request for correcting a service code (e.g., diagnosis code designated by a payer institution) associated with the claim record 711.

After the provider computing entity 102 resubmits a claim record 711 (e.g., with additional documents and/or verification), the sub-process involving the provider computing entity 102, the provider clearinghouse system 701, the processing clearinghouse system 702, and the data analysis computing entity 106 may be repeated until the processing clearinghouse system 702 determines based on the complication risk indication 721 that the claim record 711 is not risky.

If the reprocessing clearinghouse 702 determines based on the complication risk indication 721 that the claim record 711 is not risky, the processing clearinghouse system 702 transmits a payment request 732 to an insurer payment system 732. After successfully processing the payment request 732, the insurer payment system 703 requests medical services from a medical service provider system 742 that correspond to the claim record 711. This may result in closing a gap in service due to an unpaid claim.

D. Post-Generation Processing of Service Records

The medical record processing system 105 may (e.g., using the inference engine 132) perform one or more operations to process a service record after generating the service record, e.g., generating the service record using the method of FIG. 4. For example, the medical record processing system 105 may assign a service code to each claim in the service record, e.g., assign an optimized diagnosis code to each claim based on a diagnosis code optimization module. The system 105 may assign service codes in accordance with historic data about past practices and policies of the payer institution and/or using a machine learning module whose parameters are trained in accordance with such historic data.

As another example, the medical record processing system 105 may present the service record to a payer institution (in a batch with other service records and/or in real-time). In some embodiments, to present the service record to a payer institution in real-time, the medical record processing system 105 transmits the service record in response to a periodic query by the payer institution computing entities and/or stores the service record in a location (e.g., a location in the knowledgebase 108) periodically queried by the payer institution computing entities.

In some embodiments, the medical record processing system 105 records the outcome of the processing of a service record by a payer institution, e.g., in the knowledgebase 108. For example, if an insurance company rejects a medical service record, the medical record processing system 105 records that data. The medical record processing system 105 may use the recorded data to generate training data for a component of the medical record processing system 105, such as the inference engine 132.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, the foregoing description provides various examples of utilizing systems and methods for monitoring cognitive capability of a user. However, it should be understood that various embodiments of the systems and methods discussed herein may be utilized for providing reminders of any activity, such as exercising, eating healthy snacks, performing a particular task, calling another individual, and/or the like.

The invention claimed is:

1. A computer-implemented method for generating a collaborative record, the method comprising:
   receiving a free-form primary provider input originating from a primary provider computing entity, wherein the free-form primary provider input comprises a plurality of unstructured data elements and is associated with a primary provider profile;
   detecting, based at least in part on stored informational requirements data, discrete data elements within the unstructured data elements of the free-form primary provider input and one or more information deficiencies in the primary provider input, wherein each information deficiency indicates a respective query;
   for each identified information deficiency of the one or more information deficiencies,
      identifying a supportive profile associated with the respective information deficiency, wherein the supportive profile is associated with a respective computing profile;
      causing the supportive profile computing entity associated with the respective supportive profile to present an audiovisual interface, wherein the audiovisual interface includes an indication of the respective query associated with the information deficiency; and
      receiving a supportive provider input originating from the supportive profile computing entity associated with the respective supportive profile; and
   generating the collaborative record for the primary provider input based at least in part on the primary provider input and each received supportive provider input.

2. The computer-implemented method of claim 1, further comprising:
   identifying one or more service units associated with the primary provider input; and
   determining a complication risk indication for each service unit of the one or more service units, wherein the complication risk indication associated with a service unit denotes a likelihood that the service unit will face a complicating condition in the future; and
   wherein generating the collaborative record is performed based at least in part on each complication risk indication for a service unit of the one or more service units.

3. The computer-implemented method of claim 2, wherein determining the complication risk indication for a service unit comprises:
   identifying one or more risk attributes associated with the service unit, wherein the one or more risk attributes include a service code associated with the service unit; and
   determining an individual complication risk score for each risk attribute of the one or more risk attributes;

determining an overall complication risk score for the service unit based at least in part on each individual complication risk for a risk attribute of the one or more risk attributes; and determining the complication risk indication for the service unit based at least in part on the overall complication risk score for the service unit.

4. The computer-implemented method of claim 2, wherein generating the collaborative record based at least in part on each complication risk indication for a service unit of the one or more service units comprises:

for each service unit of the one or more service units,
determining whether the complication risk indication for the service unit indicates that the service unit is risky;
in response to determining that the complication risk indication for the service unit indicates that the service unit is risky, preventing inclusion of the service unit in the collaborative record; and
in response to determining that the complication risk indication for the service unit indicates that the service unit is not risky, causing inclusion of the service unit in the collaborative record.

5. The computer-implemented method of claim 1, wherein detecting the one or more information deficiencies in the primary provider input comprises:

identifying one or more service units associated with the primary provider input;
for each service unit of the one or more service units,
identifying one or more existing attributes for the service unit originating from the discrete data elements; and
identifying one or more required attributes for the service unit originating from the informational requirements data; and
detecting the one or more information deficiencies by comparing the one or more required attributes for each service unit of the one or more service units with the corresponding one or more existing attributes for the service unit.

6. The computer-implemented method of claim 5, wherein identifying the one or more required attributes associated with a service unit comprises:

determining a complication risk indication associated with the service unit, wherein the complication risk indication denotes a likelihood that the service unit will face a complicating condition in the future; and
querying the informational requirements data based at least in part on the complication risk indication associated with the service unit to retrieve the one or more required attributes associated with the service unit.

7. The computer-implemented method of claim 1, wherein the audiovisual interface includes an audio element.

8. The computer-implemented method of claim 7, wherein the audio element is generated using speech synthesis.

9. The computer-implemented method of claim 1, wherein causing a supportive profile computing entity associated with a supportive profile to present an audiovisual interface comprises:

determining an availability time for the supportive profile; and
causing the supportive profile computing entity to present the audiovisual interface at the availability time.

10. An apparatus for generating a collaborative record, the apparatus comprising at least one processor and at least one memory including program code, the at least one memory and the program code configured to, with the processor, cause the apparatus to at least:

receive a free-form primary provider input originating from a primary provider computing entity, wherein the free-form primary provider input comprises a plurality of unstructured data elements and is associated with a primary provider profile;
detect, based at least in part on stored informational requirements data, discrete data elements within the unstructured data elements of the free-form primary provider input and one or more information deficiencies in the primary provider input, wherein each information deficiency indicates a respective query;
for each identified information deficiency of the one or more information deficiencies,
identify a supportive profile associated with the respective information deficiency, wherein the supportive profile is associated with a respective computing profile;
cause the supportive profile computing entity associated with the respective supportive profile to present an audiovisual interface, wherein the audiovisual interface includes an indication of the respective query associated with the information deficiency; and
receive a supportive provider input originating from the supportive profile computing entity associated with the respective supportive profile; and
generate the collaborative record for the primary provider input based at least in part on the primary provider input and each received supportive provider input.

11. The apparatus of claim 10, wherein the at least one memory and the program code are further configured to, with the processor, cause the apparatus to at least:

identify one or more service units associated with the primary provider input; and
determine a complication risk indication for each service unit of the one or more service units, wherein the complication risk indication associated with a service unit denotes a likelihood that the service unit will face a complicating condition in the future; and
wherein generating the collaborative record is performed based at least in part on each complication risk indication for a service unit of the one or more service units.

12. The apparatus of claim 11, wherein determining the complication risk indication for a service unit comprises:

identifying one or more risk attributes associated with the service unit, wherein the one or more risk attributes include a service code associated with the service unit; and
determining an individual complication risk score for each risk attribute of the one or more risk attributes;
determining an overall complication risk score for the service unit based at least in part on each individual complication risk for a risk attribute of the one or more risk attributes; and
determining the complication risk indication for the service unit based at least in part on the overall complication risk score for the service unit.

13. The apparatus of claim 11, wherein generating the collaborative record based at least in part on each complication risk indication for a service unit of the one or more service units comprises:

for each service unit of the one or more service units, determining whether the complication risk indication for the service unit indicates that the service unit is risky;

in response to determining that the complication risk indication for the service unit indicates that the service unit is risky, preventing inclusion of the service unit in the collaborative record; and in response to determining that the complication risk indication for the service unit indicates that the service unit is not risky, causing inclusion of the service unit in the collaborative record.

14. The apparatus of claim 10, wherein detecting the one or more information deficiencies in the primary provider input comprises:

identifying one or more service units associated with the primary provider input;

for each service unit of the one or more service units,
identifying one or more existing attributes for the service unit originating from the discrete data elements; and
identifying one or more required attributes for the service unit originating from the informational requirements data; and detecting the one or more information deficiencies by comparing the one or more required attributes for each service unit of the one or more service units with the corresponding one or more existing attributes for the service unit.

15. The apparatus of claim 14, wherein identifying the one or more required attributes associated with a service unit comprises:

determining a complication risk indication associated with the service unit, wherein the complication risk indication denotes a likelihood that the service unit will face a complicating condition in the future; and querying the informational requirements data based at least in part on the complication risk indication associated with the service unit to retrieve the one or more required attributes associated with the service unit.

16. The apparatus of claim 10, wherein the audiovisual interface includes an audio element.

17. The apparatus of claim 16, wherein the audio element is generated using speech synthesis.

18. A non-transitory computer-readable storage medium for generating a collaborative record, the computer-readable storage medium storing program code instructions that, when executed, cause a computing device to:

receive a free-form primary provider input originating from a primary provider computing entity, wherein the free-form primary provider input comprises a plurality of unstructured data elements and is associated with a primary provider profile;

detect, based at least in part on stored informational requirements data, discrete data elements within the unstructured data elements of the free-form primary provider input and one or more information deficiencies in the primary provider input, wherein each information deficiency indicates a respective query;

for each identified information deficiency of the one or more information deficiencies,
identify a supportive profile associated with the respective information deficiency, wherein the supportive profile is associated with a respective computing profile;
cause the supportive profile computing entity associated with the respective supportive profile to present an audiovisual interface, wherein the audiovisual interface includes an indication of the respective query associated with the information deficiency; and
receive a supportive provider input originating from the supportive profile computing entity associated with the respective supportive profile; and generate a collaborative record for the primary provider input based at least in part on the primary provider input and each received supportive provider input.

19. The non-transitory computer-readable storage medium of claim 18, wherein the program code instructions, when executed, further cause the computing device to:

identify one or more service units associated with the primary provider input; and determine a complication risk indication for each service unit of the one or more service units, wherein the complication risk indication associated with a service unit denotes a likelihood that the service unit will face a complicating condition in the future; and wherein generating the collaborative record is performed based at least in part on each complication risk indication for a service unit of the one or more service units.

* * * * *